United States Patent
Rains et al.

(10) Patent No.: US 9,381,031 B2
(45) Date of Patent: Jul. 5, 2016

(54) SURGICAL INSTRUMENTS FOR CUTTING CAVITIES IN INTRAMEDULLARY CANALS

(75) Inventors: James K. Rains, Cordova, TN (US); Brian L. Black, Southaven, MS (US)

(73) Assignee: Smith & Nephew, Inc., Memphis, TN (US)

( * ) Notice: Subject to any disclaimer, the term of this patent is extended or adjusted under 35 U.S.C. 154(b) by 1091 days.

(21) Appl. No.: 13/386,779

(22) PCT Filed: Jul. 23, 2010

(86) PCT No.: PCT/US2010/043018
§ 371 (c)(1),
(2), (4) Date: Mar. 27, 2012

(87) PCT Pub. No.: WO2011/011664
PCT Pub. Date: Jan. 27, 2011

(65) Prior Publication Data
US 2012/0179161 A1    Jul. 12, 2012

Related U.S. Application Data (60) Provisional application No. 61/228,252, filed on Jul. 24, 2009.

(51) Int. Cl.
| | |
|---|---|
| *A61B 17/16* | (2006.01) |
| *A61B 17/32* | (2006.01) |
| *A61B 17/3207* | (2006.01) |
| *A61B 17/00* | (2006.01) |

(52) U.S. Cl.
CPC ......... *A61B 17/32002* (2013.01); *A61B 17/164* (2013.01); *A61B 17/1617* (2013.01); *A61B 17/1631* (2013.01); *A61B 17/320725* (2013.01); *A61B 2017/00526* (2013.01); *A61B 2017/320032* (2013.01); *A61B 2217/005* (2013.01); *A61B 2217/007* (2013.01)

(58) Field of Classification Search
CPC .... A61B 17/32; A61B 17/1615; A61B 17/16; A61B 17/164
See application file for complete search history.

(56) References Cited

U.S. PATENT DOCUMENTS

| | | | | |
|---|---|---|---|---|
| 18,003 | A | * | 4/1891 | Weeks .......................... 408/156 |
| 450,323 | A | * | 4/1891 | Tomlinson ................. 15/104.19 |
| 1,038,914 | A | * | 9/1912 | Long .............................. 408/82 |
| 1,126,961 | A | * | 2/1915 | Denney ........................... 82/1.2 |

(Continued)

FOREIGN PATENT DOCUMENTS

| | | |
|---|---|---|
| CN | 1845709 A | 10/2006 |
| DE | 2542056 A1 | 3/1977 |
| WO | WO2007057902 A3 | 7/2007 |

OTHER PUBLICATIONS

Office Action for Russian Application No. 2012105452/14, mailed Jul. 30, 2014.

(Continued)

*Primary Examiner* — Christian Sevilla
(74) *Attorney, Agent, or Firm* — Fish & Richardson P.C.

(57) ABSTRACT

Surgical instruments and procedures are disclosed that enable the injection of an optimal amount of curable resin and/or the placement of an internal fixation device in an intramedullary canal of a fractured bone. The disclosed instruments and procedures enable a surgeon to clear a portion of the canal of cancellous bone and marrow across the fracture site without damaging the cortical wall.

34 Claims, 5 Drawing Sheets

(56) References Cited

U.S. PATENT DOCUMENTS

| | | | | |
|---|---|---|---|---|
| 1,424,268 | A | * | 8/1922 | Vedoe .......................... 408/164 |
| 1,562,327 | A | * | 11/1925 | Hedeen ...................... 15/104.09 |
| 1,685,380 | A | * | 9/1928 | Shultz ........................ 15/104.19 |
| 1,721,106 | A | * | 7/1929 | Fischbeck .................. 15/104.19 |
| 1,733,827 | A | * | 10/1929 | Seiler .......................... 408/200 |
| 1,786,520 | A | * | 12/1930 | Darling ...................... 15/104.19 |
| 2,599,077 | A | * | 6/1952 | Sturgis ....................... 15/104.09 |
| 3,076,254 | A | * | 2/1963 | Ricci ........................... 408/200 |
| 3,278,964 | A | * | 10/1966 | Horelica ..................... 15/236.01 |
| 3,320,957 | A | * | 5/1967 | Sokolik ....................... 606/180 |
| 3,442,162 | A | * | 5/1969 | Cogsdill ...................... 408/156 |
| 3,917,429 | A | * | 11/1975 | Ertley .......................... 408/227 |
| 4,256,510 | A | * | 3/1981 | Thompson et al. ................. 134/6 |
| 4,473,070 | A | * | 9/1984 | Matthews et al. ............. 606/80 |
| 5,297,905 | A | * | 3/1994 | Schmidt et al. .............. 408/145 |
| 5,658,103 | A | * | 8/1997 | Inokuchi et al. ............. 408/145 |
| 5,690,634 | A | * | 11/1997 | Muller et al. .................... 606/80 |
| 5,885,258 | A | * | 3/1999 | Sachdeva et al. ............. 604/530 |
| 5,891,148 | A | * | 4/1999 | Deckner ........................ 606/80 |
| 5,938,379 | A | * | 8/1999 | Tseng ........................... 408/199 |
| 6,152,814 | A | * | 11/2000 | Amarosa et al. ............. 451/526 |
| 6,440,138 | B1 | * | 8/2002 | Reiley et al. .................... 606/79 |
| 7,523,946 | B2 | * | 4/2009 | Schmitt ........................ 279/2.22 |
| 8,287,538 | B2 | * | 10/2012 | Brenzel et al. .................. 606/62 |
| 2004/0092946 | A1 | | 5/2004 | Bagga et al. |
| 2005/0113836 | A1 | * | 5/2005 | Lozier et al. .................... 606/80 |
| 2005/0203527 | A1 | * | 9/2005 | Carrison et al. ................. 606/80 |
| 2006/0184192 | A1 | * | 8/2006 | Markworth et al. .......... 606/198 |
| 2007/0049860 | A1 | * | 3/2007 | Seminara .......................... 604/1 |
| 2007/0060933 | A1 | * | 3/2007 | Sankaran et al. ............. 606/160 |
| 2008/0009876 | A1 | * | 1/2008 | Sankaran et al. ............... 606/84 |
| 2008/0221608 | A1 | * | 9/2008 | Betts ............................ 606/191 |
| 2009/0177206 | A1 | | 7/2009 | Lozier et al. |
| 2011/0190803 | A1 | * | 8/2011 | To et al. ....................... 606/180 |
| 2013/0261628 | A1 | * | 10/2013 | Burley et al. .................... 606/80 |

OTHER PUBLICATIONS

Authorized Officer Kim Jun Gyu, International Search Report/Written Opinion in PCT/US2010/043018, mailed Mar. 29, 2011, 10 pages.
First Office Action for Chinese Application No. 201080032964.4, mailed Dec. 20, 2013, with English translation.
Second Office Action for Chinese Application No. 201080032964.4, mailed Nov. 14, 2014, with English translation.
Third Office Action for Chinese Application No. 201080032964.4, mailed Aug. 5, 2015, with English synopsis.
Rodgers, M.M., and Cavanagh, P.R., "Glossary of Biomechanical Terms, Concepts, and Units," Physical Therapy, col. 64, No. 12, Dec. 1984.
Extended European Search Report for European Application No. 10802938.0, mailed Sep. 5, 2013.
Communication Pursuant to Article 94(3) EPC for European Application No. 10802938.0, mailed Sep. 17, 2014.
Communication Pursuant to Article 94(3) EPC for European Application No. 10802938.0, mailed Jul. 13, 2015.
Office Action for Russian Application No. 2012105452/14(008317), mailed Jul. 10, 2015, with English-language Summary.

* cited by examiner

SURGICAL INSTRUMENTS FOR CUTTING CAVITIES IN INTRAMEDULLARY CANALS

CROSS REFERENCE TO RELATED APPLICATION

This application claims priority to and the full benefit of U.S. Provisional Application Ser. No. 61/228,252, filed Jul. 24, 2009, and titled "Surgical Instruments For Cutting Cavities in Intramedullary Canals," the entire contents of which are incorporated herein by reference.

TECHNICAL FIELD

Surgical instruments and procedures are disclosed for selectively forming cavities in intramedullary (IM) canals of bones.

BACKGROUND

For purposes of this disclosure, the anatomy of a bone of a human or mammal can be divided into three principal segments: (1) the outer cortical bone that provides a rigid outer structure and weight bearing capabilities of the bone; (2) cancellous bone tissue disposed between the cortical bone and the intramedullary (IM) canal; and (3) the IM canal that passes axially through the cortical bone and cancellous bone tissue. Cancellous bone is substantially weaker than cortical bone. The boundary between the cancellous bone and the outer cortical bone structure is often referred to as the cortical wall.

Certain bone fractures are repaired surgically by clearing a cavity in the IM canal of the fractured bone that traverses the fracture site and installing a filler material and/or other structures in the cavity. Surgical instruments are available for forming such cavities in vertebrae. For example, some instruments include an expandable body or balloon for forming a cavity in the cancellous bone tissue of vertebrae. The expandable body or balloon compresses the cancellous bone to form the cavity. The cavity receives the filler material, which provides interior structural support for cortical bone while the cortical bone heals. Because such devices are not intended to cut bone, at least a small cavity must be cut or otherwise formed in the cancellous bone in a separate procedure in order to initially insert the balloon-like device.

It is frequently desirable to form a larger cavity in an IM canal and cancellous bone than can be formed with devices designed to compress and/or displace cancellous bone or material disposed in the IM canal, rather than cutting and removing such material. However, the concept of cutting and removing cancellous bone without damaging the cortical wall or cortical bone structure is problematic. Specifically, the diameters of IM canals and cortical walls are not constant, but highly irregular and non-circular. The IM canal and cortical wall often have oblong profiles that vary in dimension and geometry not only from individual to individual, but also along the length of a bone axis. As a result, drilling cancellous bone with a conventional surgical drill or a rotating cutting tool can cause damage to the cortical wall, especially along narrower portions of an IM canal and cortical wall.

Further, as cancellous bone is much weaker than cortical bone, conventional drilling instruments used in the IM canal have the potential to quickly drill through cancellous bone before unintentionally reaching the cortical wall and surrounding cortical bone. While one advantage of the above-described balloon compression devices is that the danger of damaging the cortical wall is minimal because cancellous bone is not cut, the above-described compression devices provide no means for forming larger cavities by cutting cancellous bone tissue safely without damaging the surrounding cortical wall. Further, the above-described balloon compression devices provide no means for removing cancellous bone tissue, which may be necessary for the formation of larger cavities within the IM canal.

In contrast, conventional drilling/reaming devices may be used to form the cavity. However, when using a conventional drilling/reaming device, the surgeon must be concerned with the pre-selected drill/reamer being too large for any part of the IM canal. If the drill/reamer is not properly selected, the cortical bone along an area where the cortical wall inner diameter is smaller than that of the drill/reamer may be unintentionally cut. Further, due to variations in the inner diameter of the cortical bone, the surgeon may be forced to select a drill bit or reamer size that is smaller than desired to avoid cutting cortical bone. As a result, the cavity may be smaller than desired.

Finally, another disadvantage to the prior art drilling/reaming devices is that an entry port for providing access to the IM canal must be axial with the IM canal. Typically, the entry port is drilled at the end of the bone through the joint. Often, this results in the removal of significant amounts of healthy cortical bone to reach the IM canal, and breaching an articular surface, which leads to joint pain. Further, if the fracture site is at an axial mid-point of the bone, more than half of the IM canal must be traversed to complete the procedure. Thus, it would be advantageous to provide a surgical instrument for forming cavities in IM canals that can utilize non-traditional entry port locations with an angled trajectory relative to the bone axis.

Accordingly, a need exists for an IM canal cavity forming device and method that can safely form cavities in IM canals without causing damage to cortical walls. There is also need for such devices that can remove cancellous bone tissue, marrow and other materials from the IM canal so that larger cavities can be formed. A need also exists for an IM canal cavity forming device that is of relatively simple construction and inexpensive to manufacture, that can be operated either manually or by a powered surgical drill, and that provides the surgeon with increased ability to create a cavity safely within the IM canal without damaging the surrounding healthy cortical bone. Further, it would be advantageous for such a device to be flexible and capable of entering the IM canal through an angled entry port, as opposed to an axial entry port at the end of the bone, i.e., through a joint.

SUMMARY OF THE DISCLOSURE

Surgical instruments and procedures are disclosed that enable the injection of an optimal amount of curable resin or putty and/or the placement of an internal fixation device including balloon/expandable devices in an IM canal of a fractured bone. The disclosed instruments enable a surgeon to clear at least a portion of the IM canal of cancellous bone and marrow across the fracture site. As a result, the surgeon can safely create a cavity for injecting or placing curable resin, putty, and/or an internal fixation device without damaging the cortical wall. The disclosed surgical instruments are able to cut cancellous bone in the IM canal without substantially damaging or cutting the cortical wall regardless of profile irregularities of the IM canal. Flexible cutting arms of the disclosed instruments are sufficiently resilient to cut cancellous material while being sufficiently elastic to deform when contacting cortical bone. The disclosed instruments may be used through an entry portal that it is not coaxial with the bone shaft or IM canal. For example, the disclosed instruments can be used with an angled trajectory of up to 45 degrees or up to 90 degrees relative to the bone axis.

In a general aspect, a surgical instrument for cutting a cavity in an intramedullary canal of a bone includes a shaft having a proximal end and a plurality of flexible cutting arms, and a distal nose section. The flexible cutting arms are formed from a shape memory material and define a relaxed effective outer diameter that is greater than effective outer diameters of the shaft and the distal nose section, the flexible cutting arms are compressible radially to a compressed effective outer diameter about equal to or less than the effective outer diameters of the shaft and distal nose section.

In another general aspect, a surgical instrument for cutting a cavity in an intramedullary canal of a bone includes a shaft comprising a proximal end and a distal end. The distal end of the shaft is coupled to a plurality of flexible helical cutting arms. The plurality of flexible helical cutting arms couple the shaft to a distal nose section. The flexible helical cutting arms are formed from a shape memory material and define a relaxed effective outer diameter that is greater than effective outer diameters of the shaft and the distal nose section. The flexible helical cutting arms are compressible radially to a compressed effective outer diameter about equal to or less than effective outer diameters of the shaft and distal nose section.

Implementations can include one or more of the following features. For example, the distal nose section includes a drill tip. The shape memory material is a shape memory alloy. The flexible cutting arms have a width, a thickness, and are characterized by a ratio of width to thickness ranging from about 5:1 to about 2:1. The flexible cutting arms are configured to cut cancellous bone and are configured to substantially not cut cortical bone. An expansion force exerted by the cutting arms when the cutting arms are released from the compressed effective outer diameter to the relaxed effective outer diameter ranges from about 1.0 lbf to about 8.0 lbf. Each flexible cutting arm is helical and rotates at an angle from between about negative 60 degrees to about 60 degrees from a longitudinal axis of the instrument. The flexible cutting arms are left-hand helical. The shaft comprises at least one of a biocompatible polymer, a steel cable and a twisted wire.

In another general aspect, a surgical instrument for cutting a cavity in an intramedullary canal of a bone includes a shaft and a plurality of flexible and helical cutting arms. The flexible and helical cutting arms are formed from a shape memory alloy and define a relaxed effective outer diameter that is greater than an effective outer diameter of the shaft. The flexible cutting arms are compressible radially to a compressed effective outer diameter about equal to or less than the effective outer diameter of the shaft. An expansion force exerted by the flexible and helical cutting arms is from about 1.0 lbf to about 8.0 lbf.

In another general aspect, a method of repairing a bone fracture, the bone comprising a cortical wall, an intramedullary canal and a fracture site, includes drilling an entry port in the bone that is spaced apart from a fracture site, the entry port providing access to an intramedullary canal of the fractured bone, the entry port having a diameter greater than effective outer diameters of a shaft and a distal nose section of a surgical instrument for forming a cavity in the intramedullary canal, compressing flexible cutting arms of the surgical instrument, inserting at least a portion of the surgical instrument into the intramedullary canal through the entry port, and forming a cavity in the intramedullary canal proximate the fracture site.

Implementations can include one or more of the following features. For example, the distal nose section comprises a drill tip and drilling the entry port in the bone comprises rotating the surgical instrument while the drill tip engages the bone. Forming the cavity comprises rotating the surgical instrument so that the flexible cutting arms cut cancellous bone, the flexible cutting arms being configured to substantially not cut cortical bone. Allowing the flexible cutting arms to expand towards a relaxed effective outer diameter within the intramedullary canal due to an expansion force applied, at least in part, by a spring effect of the material of the flexible cutting arms, the expansion force being from about 1.0 lbf to about 8.0 lbf. The expansion force is insufficient to allow the flexible cutting arms to substantially cut cortical bone. Removing material from the intramedullary canal through a lumen disposed in the shaft of the surgical instrument. Irrigating the intramedullary canal by dispensing irrigation fluid through a lumen disposed in the shaft of the surgical instrument. Withdrawing the surgical instrument through the entry port, injecting a curable resin through the entry port into the cavity, and allowing the resin to cure. The entry port is drilled in a non-articular surface of the bone, and inserting at least a portion of the surgical instrument comprises bending the shaft of the surgical instrument.

In another general aspect, a method of forming a cavity in a bone, the bone having cortical wall, cancellous bone, an intramedullary canal, and a fracture site, includes drilling an entry port in the bone that is spaced apart from the fracture site, the entry port providing access to the intramedullary canal of the fractured bone, inserting a surgical instrument through the entry port to the intramedullary canal by compressing flexible cutting arms of the surgical instrument, rotating the surgical instrument to remove cancellous bone without substantially damaging the cortical wall, and moving the surgical instrument within the intramedullary canal to create a cavity. The cavity can substantially follow the shape of the cortical wall.

The details of one or more implementations are set forth in the accompanying drawings and the description below. Other features will be apparent from the description and drawings, and from the claims.

DETAILED DESCRIPTION

Figure 1:
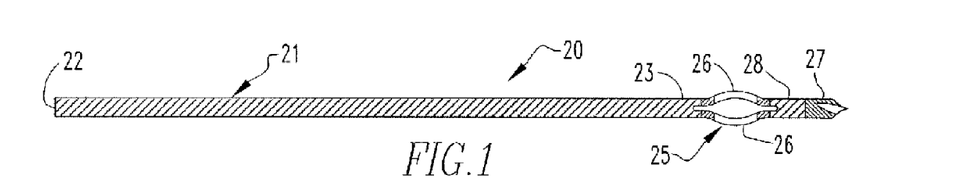
FIG. 1 is a cross-sectional view of a surgical instrument for cutting cancellous bone in an IM canal.
Figures 2, 3, 4, 5, 6, 7:
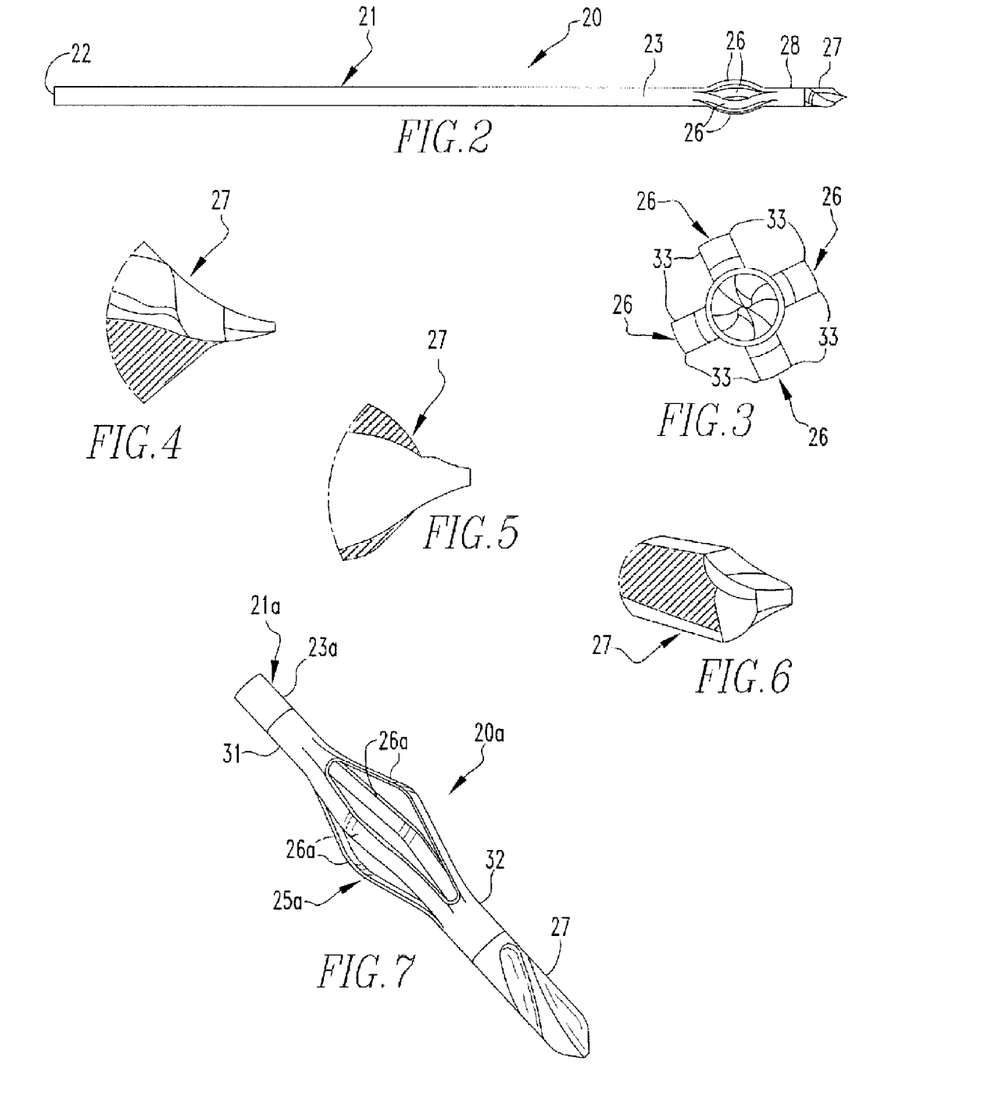
FIG. 2 is a side view of the surgical instrument of FIG. 1.
FIG. 3 is an end view of the surgical instrument of FIG. 1.
FIGS. 4-6 are enlarged detail views of an end section of the surgical instrument of FIG. 1.
FIG. 7 is a partial perspective view of the surgical instrument of FIG. 1.

Turning to FIG. 1, a surgical instrument 20 is shown that includes a flexible shaft 21 with a proximal end 22 and a distal end 23. The proximal end 22 of the shaft 21 may be coupled to a connector for connecting the shaft 21 to surgical drilling instrument, such as the drill 24 of FIG. 17. Alternatively, the proximal end 22 of the shaft 21 may be coupled to a handle or other suitable device for assisting or allowing a surgeon to rotate the instrument 20. Any of these components can also be made as an integral part of the instrument. The distal end 23 the shaft 21 may be coupled directly or indirectly to an expandable cutting device 25 which, as shown in FIGS. 1-3, includes four flexible cutting arms 26. The number of cutting arms 26 may vary but two or more cutting arms 26 are preferred. The cutting arms 26 may be coupled directly or indirectly to a distal nose section 27. For example, a distal shaft or collar section 28 may be disposed between the cutting arms 26 and the distal nose section 27. The distal nose section 27 comprises a drill tip with a brad point tip. Exemplary details of a suitable drill tip 27 for use with the instrument 20 are illustrated in FIGS. 4-6. A variety of designs for the drill tip 27 may be employed as will be apparent to those skilled in the art. The design specifics of the drill tip 27 are not essential to an understanding of this disclosure. The drill tip 27 may be used to drill an entry port 41 (FIGS. 18-19) through cortical bone which allows the expandable cutting device 25 to enter the IM canal. While the drill tip 27 is primarily used to drill an entry port 41, the drill tip 27 may also be used to remove initial amounts of cancellous bone and marrow prior to forming a cavity by rotating the instrument 20 and flexible cutting arms 26. In some implementations, the distal nose can include a trocar, spade drill, diamond point spade drill, or a half round drill.

In FIG. 7, the shaft 21a is coupled to a collar 31 at its distal end 23a. The cutting arms 26a couple the collar 31 to a distal collar 32, which, in turn, couples the expandable cutting device 25a to the distal nose section or drill tip 27. Thus, in the device 20a illustrated in FIG. 7, the shaft 21a and cutting device 25a may be fabricated or formed separately and coupled together during assembly.

Figure 21:
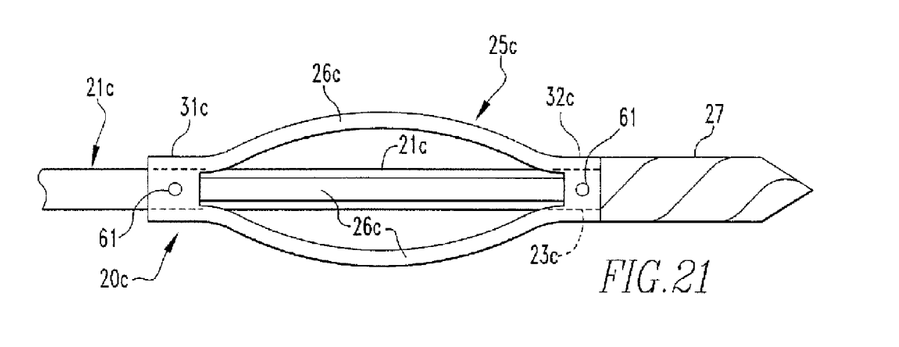
FIG. 21 is a partial view of a surgical instrument.

FIGS. 12-16 illustrate a surgical instrument 20b that has a cutting device 25b with helical arms 26b. FIG. 21 illustrates a shaft 21c that passes through the cutting arms 26c and collars 31c and 32c. Regardless of the shaft construction and the cutting device construction, the surgical instruments 20-20c include flexible shafts 21-21c that are coupled to an expandable cutting device 25-25c at distal ends 23-23c of the shafts 21-21c and a drill attachment connector or handle is coupled to the proximal ends 22 of the shafts 21-21c.

The shafts 21-21c, cutting arms 26-26c, optional collars 31, 32, 31c, 32c, optional distal shaft section 28 and optional drill tip 27 may be fabricated from a single piece of flexible material, such as a shape memory material. For example, the shaft 21 and cutting arms 26 are fabricated from a single piece of nitinol (nickel-titanium shape memory alloy (SMA)). Other suitable shape memory materials include, but are not limited to, alloys of titanium-palladium-nickel, nickel-titanium-copper, gold-cadmium, iron-zinc-copper-aluminum, titanium-niobium-aluminum, uranium-niobium, hafnium-titanium-nickel, iron-manganese-silicon, nickel-titanium, nickel-iron-zinc-aluminum, copper-aluminum-iron, titanium-niobium, zirconium-copper-zinc, and nickel-zirconium-titanium. The shape memory alloys may be suitable for the fabrication of surgical instruments for cutting cancellous bone without cutting cortical bone. Other suitable shape memory materials other than metallic alloys and polymers are possible as will be apparent to those skilled in the art. Furthermore, in some implementations with different requirements, such as where substantial radial collapse of the cutting device 25-25c and cutting arms 26-26c is not required, the arms 26-26c could be made from other metals or plastics.

The flexibility of the shafts 21-21c, is provided by a small shaft diameter and by selecting a material having a modulus of elasticity falling within a desired range. In addition to fabricating the shafts 21-21c from a shape memory alloy as described above, the shafts 21-21c may also be fabricated from a high-strength biocompatible polymer, such as polyetheretherketone (PEEK), polyethereketone (PEK), high density polyethylene (HDPE), or a polyamide such as nylon. As will be apparent to those skilled in the art, other suitable polymers are available.

The expandable cutting device 25 illustrated in FIGS. 1-3 and 7 comprises two or more expandable elongated cutting arms 26. Referring to FIGS. 1-2, the cutting arms 26 are disposed between the distal end 23 of the shaft 21 and the optional distal shaft section 28 or the distal nose section or drill tip 27. As shown in FIG. 7, the cutting arms 26 may be disposed between a pair of collars 31, 32. Alternatively, the cutting arms 26 can be coupled to a pair of collars 31a, 32a that are slidably received over the distal end 23a of a continuous shaft 21b, as illustrated in FIG. 21. In the device 20c of FIG. 21, one or more pins or other attachment mechanisms may hold the collars 31c, 32c in place on the shaft 21c.

The cutting arms 26-26c may form a cage-like structure. For some applications, the shape memory material or alloy used to fabricate the arms 26-26c should exhibit elastic properties. The designs illustrated in FIGS. 1-3, 7, 12-16, and 21 exploit the elastic properties of shape memory alloys to allow the cutting arms 26-26c expand outward upon entry in the IM canal to their original shape. The cutting arms 26-26c are also designed to be sufficiently flexible so that harder cortical bone will cause the arms to deflect in a radially-inward direction and to not cut cortical bone. In contrast, the arms 26-26c are sufficiently resilient to cut cancellous bone and other weaker materials disposed within the cortical wall.

Figure 8:
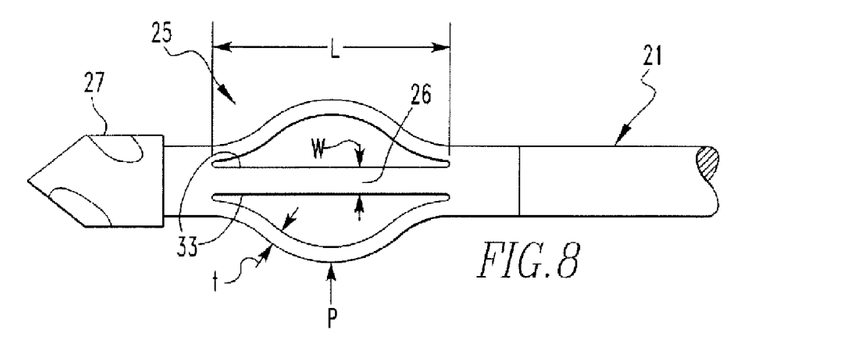
FIGS. 8 and 9 are partial side views of a surgical instrument.
Figure 9:
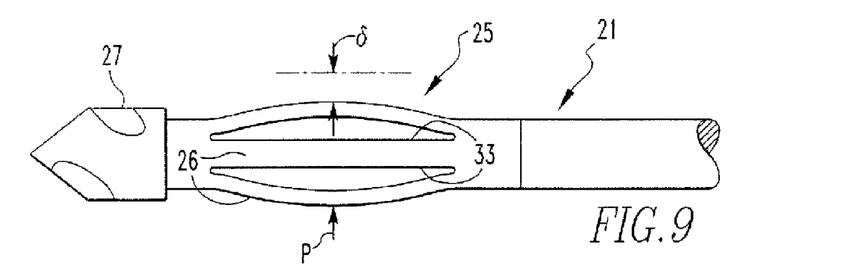

The cutting arms 26-26c can be machined using traditional techniques such as chemical etching, laser cutting, or milling, among other techniques. The cage structure of the expandable cutting devices 25-25c can be formed by placing a cutting device into a fixture that compresses the cutting arms 26-26c axially and causes the cutting arms 26-26c to expand radially outward to the desired relaxed profile or relaxed diameter (compare FIGS. 8 and 9). The fixture and cutting devices 25-25c may then be placed in an oven at a temperature of about 842° F. (450° C.) for about 15 minutes, followed by water quenching shortly after removal from the oven. This process causes the cutting arms or elements 26-26c to be shaped into a desired profile. The cutting arms 26-26c may be sharpened on at least one lateral surface 33 (FIG. 3), 33b (FIG. 16) to enable cutting of cancellous bone material. The benefit of the sharpening the cutting arms 26-26c is to provide a smoother cutting operation by reducing chatter or vibration when cutting, and by requiring a lower cutting torque.

To selectively cut cancellous bone material and not cut cortical bone material, the cutting arms must have the appropriate combination of resilience, or strength, and elasticity. Generally, the flexible cutting arms 26 should have a ratio of width (w) to thickness (t) ranging from about 5:1 to about 2:1 and ratio of length (L) to width (w) ranging from about 20:1 to about 6:1. In one example, the material of the cutting arms 26 is nitinol and the elements have a cross-sectional thickness (t) of about 0.014 in (0.356 mm), a width (w) of about 0.056 in (1.42 mm) and a length (L) of about 0.75 in (19.05 mm) (see also FIG. 8). These dimensions are an example that allow the cutting arms 26-26c to be strong enough to cut cancellous material as the cutting device 25 rotates while being flexible enough to compress radially when the arms 26-26c engage cortical bone. The dimensions will vary depending upon the anatomy or size of IM canal in which a cavity is to be formed.

Figure 10:
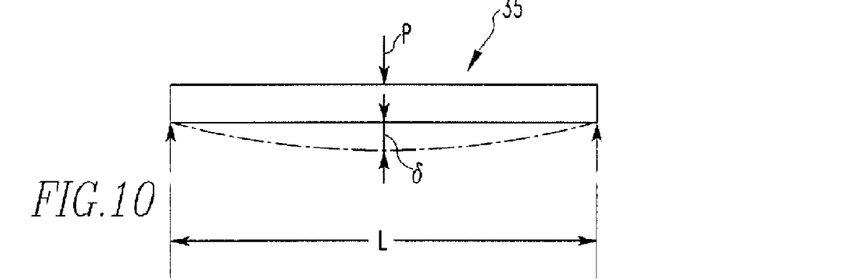
FIGS. 10 and 11 illustrate a leaf spring structure.

Additional methodologies for calculating other appropriate dimensions of the cutting arms 26-26c include consideration of moment of inertia (I), expansion force (P) and the deflection (δ) of the cutting arms 26-26c. Specifically, the behavior of the cutting arms 26-26c of the expandable cutting device 25-25c can be predicted by treating the arms 26-26c as a leaf spring 35, illustrated in FIGS. 10 and 11. The body of leaf spring 35 has a length (L), a width (w), and a thickness (t). Using a traditional beam deflection calculation, the amount of deflection (δ) can be expressed as Equation 1.

$$\delta = PL^3/48EI \tag{1}$$

Figure 11:
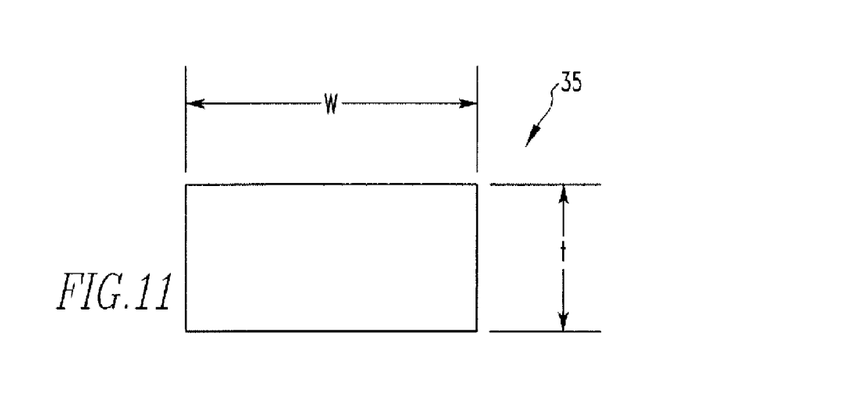
Figure 12:
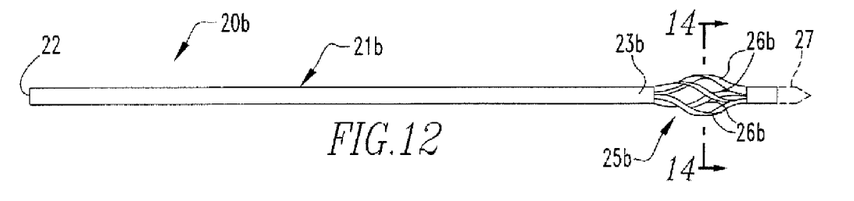
FIG. 12 is a side view of a surgical cutting device.
Figure 13:
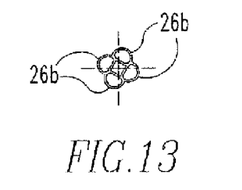
FIG. 13 is an end view of the device of FIG. 12.
Figure 14:
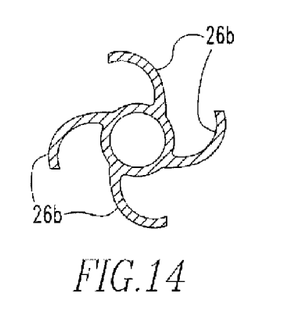
FIG. 14 is a sectional view taken along line 14-14 of FIG. 12.
Figure 15:
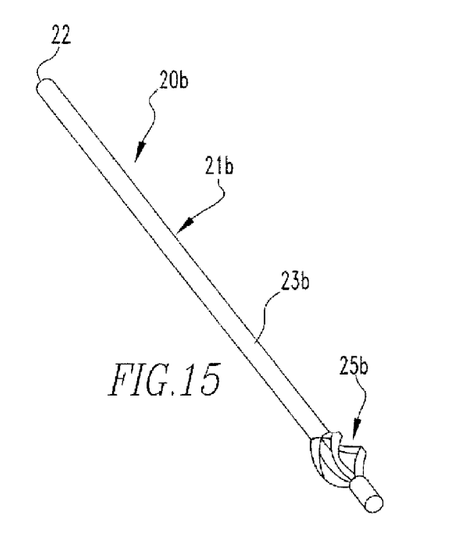
FIG. 15 is a perspective view of the surgical instrument of FIG. 12.
Figure 16:
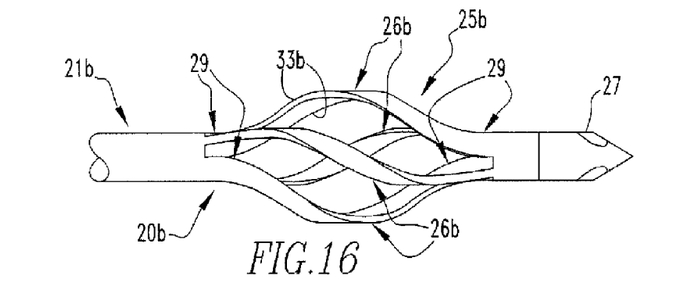
FIG. 16 is a partial side view of the surgical instrument of FIG. 12.

In equation 1, (I) is the moment of inertia and (E) is the modulus of elasticity. For nitinol, E can range from about $5.8 \times 10^6$ psi (40.0 GPa) to about $10.9 \times 10^6$ psi (75.2 GPa). Referring to FIG. 11, the moment of inertia (I) can be calculated from Equation 2.

$$I = wt^3/12 \tag{2}$$

To allow for ease of insertion of the instruments 20-20c into an IM canal, the expansion force (P) of the arms 26-26c should not be excessive. However, to expand adequately in the IM canal, the expansion force (P) must be above a minimum value. Therefore, the design of the arms 26-26c should provide an optimal expansion force (P). Through laboratory experimentation, the expansion force can range from about 1.0 lbf to about 8.0 lbf (from about 4.45 N to about 35.59 N).

By substituting Equation 2 into Equation 1 and solving for P, the expansion force (P) can be expressed as equation 3.

$$\delta = PL^3/4Ewt^3, \text{ and therefore } P = 4\delta Ewt^3/L^3 \tag{3}$$

As another example, if L=0.65 in (15.61 mm), w=0.060 in (1.52 mm), t=0.018 in (0.457 mm), and δ=0.085 in (2.16 mm), then an expansion force of P=2.51 lbf is provided by equation 3, which falls within the range of from about 1.0 lbf to about 8.0 lbf (from about 4.45 N to about 35.59 N). As δ and P are proportional when w, t, and L, are fixed, the deflection δ can be increased by about 300% by changing the size of the fixture used during the heat treatment process before P approaches the 8.0 lbf upper limit for the dimensions recited immediately above. The value of deflection δ desired in a give implementation will be dependent upon the particular bone being treated and the size of the IM canal. In other implementations, the dimensions and parameters discussed above can vary greatly, as will be apparent to those skilled in the art.

FIGS. 12-16 illustrate another surgical instrument 20b with a flexible shaft 21b having a proximal end 22 and a distal end 22. The distal end 23b of the shaft 21b is coupled to an expandable cutting device 25b with helical cutting arms 26b. The helical cutting arms 26b also include opposing sides or cutting edges 33b. The helical cutting arms 26b reduce tensile and shear stresses at the bases 29 (FIG. 16) of the cutting arm 26b so as to reduce the possibility of device failure. The helix formed by the helical cutting arms 26b can be designed to optimize the ease of cutting. The helix can be left-hand helical or right-hand helical and can be formed at an angle from about negative 60 degree to about 60 degrees from a longitudinal axis of the surgical instrument. For example, left-hand helical cutting arms in a right-hand cut may be used.

Figure 17:
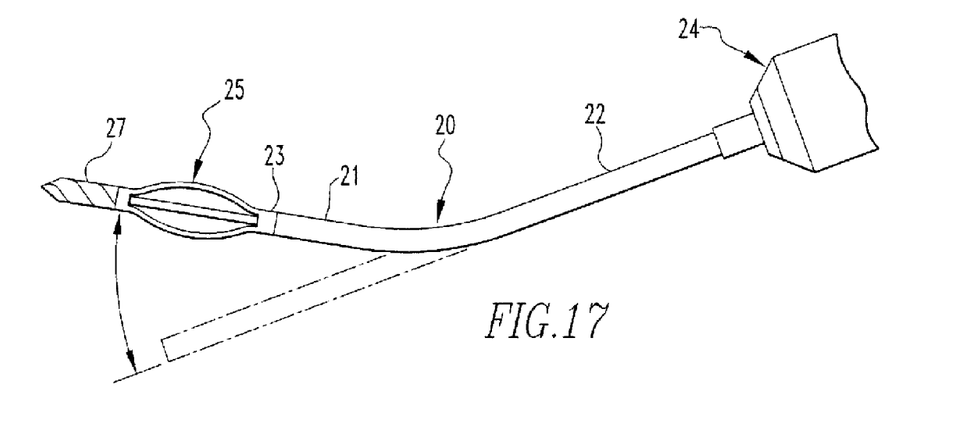
FIG. 17 illustrates a surgical instrument coupled to a surgical drill.
Figure 18:
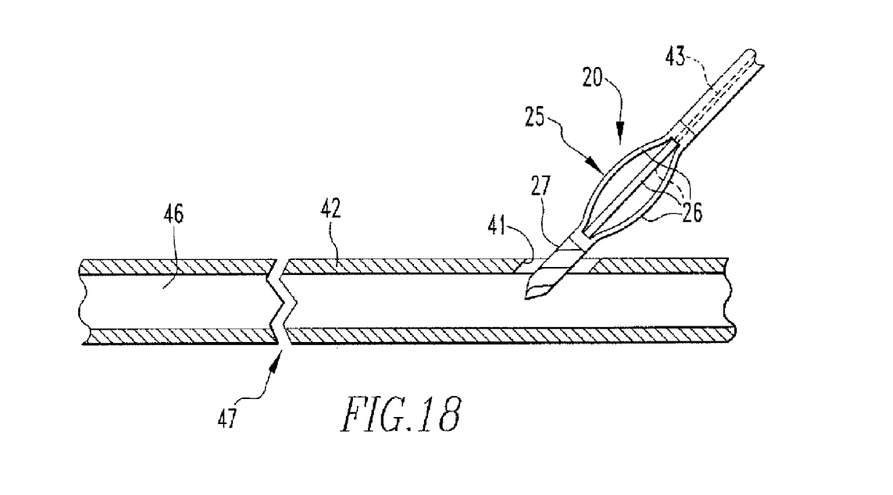
FIGS. 18 and 19 illustrate use of a surgical instrument.
Figure 19:
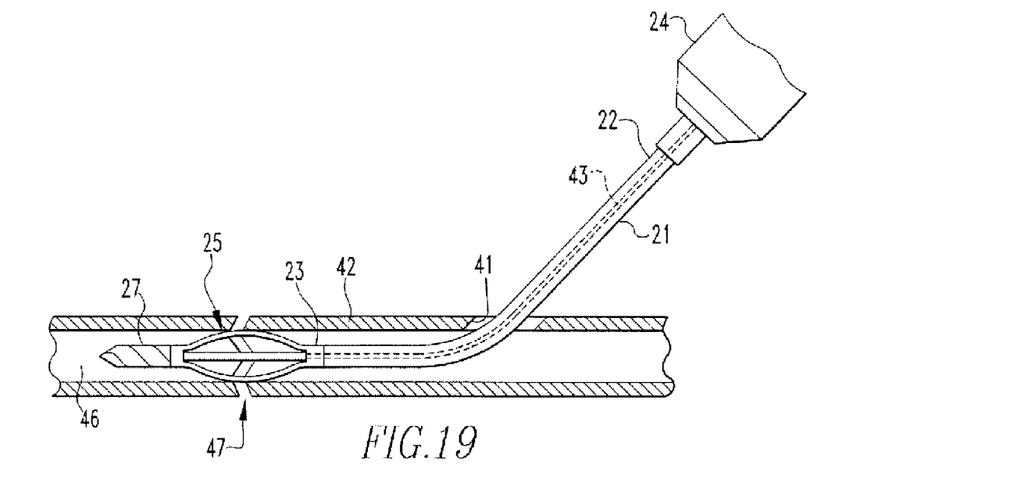
Figure 20:
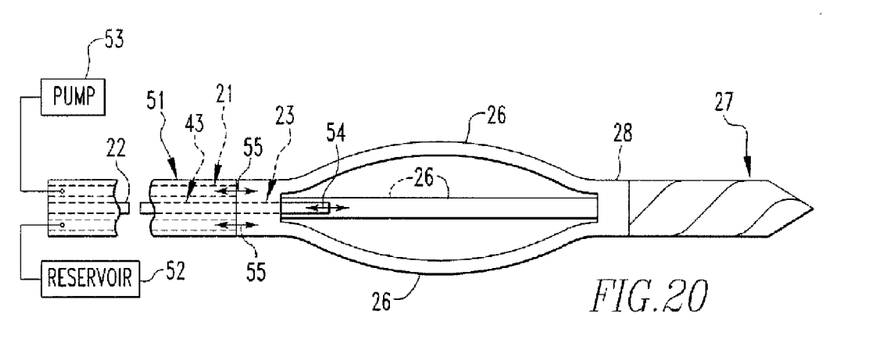
FIG. 20 illustrates a surgical instrument with multiple lumens for delivering irrigation fluid and removing cuttings.

The optional brad drill tip 27 can have a diameter that is slightly larger than a diameter of the shaft 21-21c or that is larger than a diameter of the cutting arms 26-26c when the cutting arms 26-26c are compressed. A slightly larger diameter of the drill tip 27 enables the drill tip 27 to create an entry portal 41 in cortical bone 42 to allow for passage of the remainder of the instrument 20-20c into the IM canal 46, as illustrated in FIGS. 18 and 19. The drill tip 27 will also prove useful in reaming an IM canal 46 that is smaller than expected or has an endosteal surface profile that is smaller than expected. Incorporating a drill tip 27 on the device allows for the user to create the non-axial pilot/entry hole 41 in the cortical wall 42 to gain an access portal to the IM canal 46 and fracture site 47. Thus, a separate drilling tool may not be needed to create the entry portal 41 as the proximal end 22 of the shaft 21-21c may be coupled to a surgical drill 24 as shown in FIGS. 17, 19, and 20. The tip 27 also allows for cutting a pathway in the IM canal where a minimum diameter in desired. For example, to accommodate a specific sized implant, such as a nail, the tip 27 can be used to drill a hole in the IM canal for receiving the nail.

The shafts 21-21c may include a lumen 43 (FIGS. 18-20) to allow for suction and debris removal or, alternatively, for the delivery of irrigation fluid. As shown in FIG. 20, the shaft 21 may be disposed within an outer lumen 51 that can be used for suction or for the delivery of irrigation fluid. In the embodiment illustrated in FIG. 20, the shaft 21 may also accommodate an inner lumen 43 and be disposed axially within an outer lumen 51. The outer lumen 51 and the inner lumen 43 may each be connected to a reservoir of irrigation fluid or a suction pump shown schematically at 52, 53 respectively. The bi-directional arrows 54, 55 are intended to indicate that the outer lumen 51 and inner lumen 43 can be used for either suction or irrigation or both if only a single lumen 43, 51 is utilized. A surgical drill 24 is also shown schematically in FIG. 20 that is coupled to the proximal end 22 of the shaft 21.

The components of the instruments 20-20c can be coupled to one another by a variety of means such as welding, pinning, adhesive bonds, mechanical locks (retaining ring), etc. The cutting arms 26-26c, in addition to having at least one sharpened edge 33, 33c may include serrations, relief angles, and dual sharpened edges. Further, a series of the expandable cutting devices 25-25c may be disposed along the length of the shaft 21-21c. As noted above, the cage structure of the expandable cutting device 25-25c and/or the drill tip 27 can be an integral with the shaft 21-21c.

The arms 26-26c of the disclosed cutting devices 25-25c are designed to have a high moment of inertia I in the direction of rotation and a lower moment of inertia I in the transverse radially inward direction. The disclosed designs for the arms 26-26c permit the arms 26-26c to be strong enough to cut cancellous bone in an IM canal 46 when rotating, but elastic enough in a radial direction such that when the arms 26-26c encounter a hard tissue such as cortical bone, the arms 26-26c will be deflected in a radially inward direction thereby causing no or minimal trauma to the cortical bone 42. As a result, cancellous bone in the non-symmetrical non-circular cross-sectional IM canal 46 is cut without substantial trauma or removal of cortical bone 42.

FIG. 17 illustrates the flexibility of the shaft 21 connected to the drill 24. The use of flexible but adequately stiff shafts 21-21c allows for advancement of the devices 20-20c through an IM canal 46 towards a fracture site 47 and the creation of non-traditional (i.e., non-axial) entry ports such as the one shown at 41 in FIGS. 18-19. Using a material such as reinforced PEEK or other biocompatible polymer for the shafts 21-21c, or other structures such as steel cable or twisted wire, offers an inexpensive solution as compared to other flexible shafts fabricated from nitinol, other shape memory alloys or laser cut metal shafts.

While only certain embodiments have been set forth, alternatives and modifications will be apparent from the above description to those skilled in the art. These and other alternatives are considered equivalents and within the spirit and scope of this disclosure and the appended claims.

The invention claimed is:

1. A surgical instrument for cutting a cavity in an intramedullary canal of a bone, the instrument comprising:
   a shaft having a proximal end and a plurality of flexible helical cutting arms, and a distal nose section, the flexible helical cutting arms being formed from a shape memory material and defining a relaxed effective outer diameter that is greater than effective outer diameters of the shaft and the distal nose section,
   the flexible helical cutting arms being compressible radially to a compressed effective outer diameter about equal to or less than the effective outer diameters of the shaft and distal nose section.

2. The instrument of claim 1, wherein the distal nose section includes a drill tip.

3. The instrument of claim 1, wherein the shape memory material is a shape memory alloy.

4. The instrument of claim 1, wherein the flexible helical cutting arms have a width, a thickness, and are characterized by a ratio of width to thickness ranging from about 5:1 to about 2:1.

5. The instrument of claim 4, wherein the flexible helical cutting arms are configured to cut cancellous bone and are configured to substantially not cut cortical bone.

6. The instrument of claim 1, wherein an expansion force exerted by the flexible helical cutting arms when the flexible helical cutting arms are released from the compressed effective outer diameter to the relaxed effective outer diameter ranges from about 1.0 lbf to about 8.0 lbf.

7. The instrument of claim 6, wherein the flexible helical cutting arms are configured to cut cancellous bone and are configured to substantially not cut cortical bone.

8. The instrument of claim 6, wherein the flexible helical cutting arms have a width, a thickness, and are characterized by a ratio of width to thickness ranging from about 5:1 to about 2:1.

9. The instrument of claim 1, wherein each flexible helical cutting arm rotates at an angle from between about negative 60 degrees to about 60 degrees from a longitudinal axis of the instrument.

10. The instrument of claim 9, wherein an expansion force exerted by the flexible helical cutting arms when the flexible helical cutting arms are released from the compressed effective outer diameter to the relaxed effective outer diameter ranges from about 1.0 lbf to about 8.0 lbf.

11. The instrument of claim 9, wherein the flexible helical cutting arms have a width, a thickness and are characterized by a ratio of width to thickness ranging from about 5:1 to about 2:1.

12. The instrument of claim 9, wherein the flexible helical cutting arms are configured to cut cancellous bone and are configured to substantially not cut cortical bone.

13. The instrument of claim 9, wherein the shape memory material is a shape memory alloy.

14. The instrument of claim 1, wherein the flexible helical cutting arms are left-hand helical.

15. The instrument of claim 1, wherein the shaft comprises at least one of a biocompatible polymer, a steel cable and a twisted wire.

16. A surgical instrument for cutting a cavity in an intramedullary canal of a bone, the instrument comprising:
   a shaft comprising a proximal end and a distal end, the distal end of the shaft being coupled to a plurality of flexible helical cutting arms, the plurality of flexible helical cutting arms coupling the shaft to a distal nose section,
   the flexible helical cutting arms being formed from a shape memory material and defining a relaxed effective outer diameter that is greater than effective outer diameters of the shaft and the distal nose section, the flexible helical cutting arms being compressible radially to a compressed effective outer diameter about equal to or less than effective outer diameters of the shaft and distal nose section.

17. The instrument of claim 16, wherein the distal nose section includes a drill tip.

18. The instrument of claim 16, wherein the shape memory material is a shape memory alloy.

19. The instrument of claim 16, wherein the flexible helical cutting arms have a width and a thickness, and are characterized by a ratio of width to thickness ranging from about 5:1 to about 2:1.

20. The instrument of claim 16, wherein an expansion force exerted by the flexible helical cutting arms when the flexible helical cutting arms are released from the compressed effective outer diameter to the relaxed effective outer diameter ranges from about 1.0 lbf to about 8.0 lbf.

21. The instrument of claim 16, wherein the flexible helical cutting arms are configured to cut cancellous bone and are configured to substantially not cut cortical bone.

22. The instrument of claim 16, wherein the flexible helical cutting arms are left-hand helical.

23. The instrument of claim 16, wherein the shaft comprises at least one of a biocompatible polymer, a steel cable and a twisted wire.

24. A surgical instrument for cutting a cavity in an intramedullary canal of a bone, the instrument comprising:
   a shaft; and
   a plurality of flexible and helical cutting arms, the flexible and helical cutting arms being formed from a shape memory alloy and defining a relaxed effective outer diameter that is greater than an effective outer diameter of the shaft, the flexible cutting arms being compressible radially to a compressed effective outer diameter about equal to or less than the effective outer diameter of the shaft,
   wherein an expansion force exerted by the flexible and helical cutting arms is from about 1.0 lbf to about 8.0 lbf.

25. The instrument of claim 24, wherein the instrument further comprises a distal nose section includes a drill tip.

26. The instrument of claim 24, wherein the flexible helical cutting arms have a width and a thickness, and are characterized by a ratio of width to thickness ranging from about 5:1 to about 2:1.

27. The instrument of claim 24, wherein the expansion force is an expansion force exerted by the flexible helical cutting arms when the flexible helical cutting arms are released from the compressed effective outer diameter to the relaxed effective outer diameter.

28. The instrument of claim 24, wherein the flexible helical cutting arms are configured to cut cancellous bone and are configured to substantially not cut cortical bone.

29. The instrument of claim 24, wherein the flexible helical cutting arms are left-hand helical.

30. The instrument of claim 24, wherein the shaft comprises a twisted wire.

31. The instrument of claim 24, wherein the shaft comprises a biocompatible polymer.

32. The instrument of claim 24, wherein the shaft comprises a steel cable.

33. The instrument of claim 24, wherein each flexible helical cutting arm rotates at an angle from between about negative 60 degrees to about 60 degrees from a longitudinal axis of the instrument.

34. The instrument of claim 16, wherein each flexible helical cutting arm rotates at an angle from between about negative 60 degrees to about 60 degrees from a longitudinal axis of the instrument.

* * * * *